US00PP29330P3

(12) United States Plant Patent
Stemkens

(10) Patent No.: US PP29,330 P3
(45) Date of Patent: May 29, 2018

(54) ***SAXIFRAGA* PLANT NAMED 'SAXZ0014'**

(50) Latin Name: *Saxifraga×arendsii*
Varietal Denomination: SAXZ0014

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 15/330,081

(22) Filed: Aug. 3, 2016

(65) Prior Publication Data

US 2017/0135267 P1 May 11, 2017

Related U.S. Application Data

(60) Provisional application No. 62/252,750, filed on Nov. 9, 2015.

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

(56) References Cited

PUBLICATIONS

PLUTO: Plant variety database, Sep. 9, 2017, citation for 'Saxz0014'. 1 page.*

* cited by examiner

*Primary Examiner* — Susan McCormick Ewoldt
*Assistant Examiner* — Karen M Redden
(74) *Attorney, Agent, or Firm* — Dale Skalla

(57) ABSTRACT

A new *Saxifraga* plant named 'SAXZ0014' particularly distinguished by its quite early flowering of red flowers uniformly standing above a compact plant.

1 Drawing Sheet

Latin name of the genus and species of the plant claimed: *Saxifraga×arendsii.*

Varietal denomination: 'SAXZ0014'.

BACKGROUND OF THE NEW PLANT

The present invention comprises a new *Saxifraga*, botanically known as *Saxifraga×arendsii*, and hereinafter referred to by the variety name 'SAXZ0014'.

'SAXZ0014' is a product of a planned breeding program. The new cultivar 'SAXZ0014' has red colored flowers with green leaves on a mounding compact and well branched plant.

'SAXZ0014' originates from a hybridization made in a greenhouse in April 2010 in Enkhuizen, The Netherlands. The female parent was an unpatented, proprietary plant identified as 'N0838-53', with smaller leaves and bigger flowers and late to flower when compared to 'SAXZ0014'.

The male parent of 'SAXZ0014' was an unpatented, proprietary plant identified as 'N0838-51', with smaller leaves and more star shaped flower pattern and earlier to flower when compared to 'SAXZ0014'. The resultant seed was sown in August 2010 in Enkhuizen, The Netherlands.

'SAXZ0014' was selected as one flowering plant within the progeny of the stated cross in March 2011 in a greenhouse in Enkhuizen, The Netherlands.

The first act of asexual reproduction of 'SAXZ0014' was accomplished when vegetative cuttings were propagated from the initial selection in March 2011 in a greenhouse in Enkhuizen, The Netherlands.

BRIEF SUMMARY OF INVENTION

Horticultural examination of plants grown from cuttings of the plant initiated in March 2011 in Enkhuizen, The Netherlands, and continuing thereafter, has demonstrated that the combination of characteristics as herein disclosed for 'SAXZ0014' are firmly fixed and are retained through successive generations of asexual reproduction.

'SAXZ0014' has not been observed under all possible environmental conditions. The phenotype may vary significantly with variations in environment such as temperature, light intensity and day length.

A Plant Breeder's Right for this cultivar was applied for in the European Union on Jul. 15, 2015, No. 2015/1543. 'SAXZ0014' has not been made publicly available prior to the effective filing date of this application, notwithstanding any disclosure that may have been made less than one year prior to the effective filing date of this application by the inventor or another who obtained 'SAXZ0014' directly from the inventor.

The following traits have been repeatedly observed and are determined to be basic characteristics of the new variety. The combination of these characteristics distinguishes this *Saxifraga* as a new and distinct variety.

BRIEF DESCRIPTION OF THE PHOTOGRAPHS

The accompanying photographic drawings show typical flower and foliage characteristics of 'SAXZ0014' with colors being as true as possible with an illustration of this type.

Figure 1:
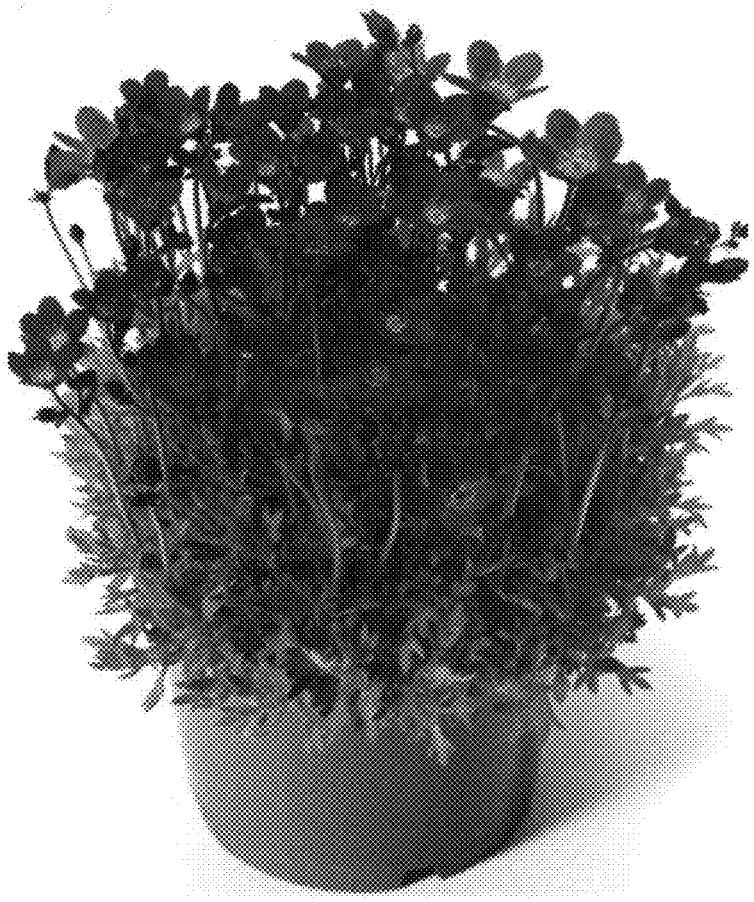
Figure 2:
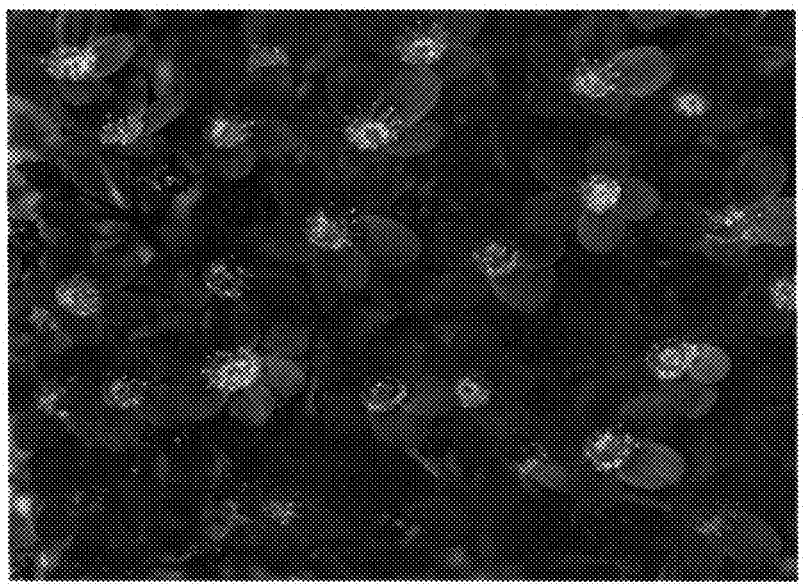

The photographic drawings show in FIG. 1 a flowering plant of the new variety and in FIG. 2 a close-up of the flowers.

DETAILED BOTANICAL DESCRIPTION

The plant descriptions and measurements were taken in Enkhuizen, The Netherlands under natural light in March 2015. These plants were approximately 36 weeks old and were growing in 11 cm pots in poly covered tunnels outdoors. The plants used for the photographs were about 36 weeks old growing in Enkhuizen, The Netherlands and the photographs were taken in March 2015.

Color chart used: Royal Horticultural Society Colour Chart (R.H.S.) 2001

TABLE 1

DIFFERENCES BETWEEN THE NEW VARIETY 'SAXZ0014' AND A SIMILAR VARIETY

| | 'SAXZ0014' | 'ROCKRED', U.S. Plant Pat. No. 19,301 |
|---|---|---|
| Flowering: | Earlier | Later |
| Plant habit: | Compact | Too compact, slow growth, |
| Leaf shape: | Thick, broad | Thin, narrow |

Plant:

*Form, growth and habit.*—A rosetting habit that is compact and mounded. Each rosette develops several short branched peduncles that are freely flowering.

*Plant height.*—6 cm.

*Plant height (inflorescence included).*—9 cm.

*Plant width.*—18 cm.

Roots:

*Number of days to initiate roots.*—About 7 days at 18 degrees C.

*Number of days to produce a rooted cutting.*—3 weeks at 18 degrees C.

*Type.*—Fine, fibrous, very well branched.

*Color.*—RHS N155B but whiter.

Foliage:

*Arrangement.*—Rosulate, alternate.

*Immature, leaf color, upper surface.*—RHS 140B.

*Immature, leaf color, lower surface.*—RHS 143A.

*Mature, leaf color, upper surface.*—RHS 141A.

*Mature, leaf color, lower surface.*—RHS 143A.

*Length.*—1.5 cm.

*Width.*—1 cm.

*Shape.*—Cunneate; 3 to 5 cleft-lobed.

*Base shape.*—Attenuate, sessile.

*Apex shape.*—Tridentate.

*Margin.*—Entire, laciniate.

*Texture, upper surface.*—Hirsute.

*Texture, lower surface.*—Glabrous.

*Color of veins, upper surface.*—Indistinct.

*Color of veins, lower surface.*—Indistinct.

*Petiole color.*—RHS 143C.

*Length.*—1.5 cm.

*Diameter.*—0.1-0.2 cm.

*Texture.*—Hirsute.

Lateral branching:

*Color.*—RHS 142B.

*Length of branch.*—1.5-2.0 cm.

*Diameter of branch.*—0.1-0.2 cm.

*Texture.*—Hirsute.

*Color of peduncle.*—RHS 142B.

*Length of peduncle.*—6.0-9.0 cm.

*Peduncle diameter.*—0.1 cm.

*Texture.*—Glandular and puberulous.

*Pedicel color.*—RHS 144A.

*Pedicel length.*—2.0 cm.

*Pedicel diameter.*—0.1 cm.

*Pedicel texture.*—Glandular and puberulous.

Inflorescence:

*Type.*—Simple cyme or raceme, each inflorescence consists of 10-15 single flowers; single flower composed of 5 imbricate petals; flowers held above the plant.

*Quantity of inflorescences per plant.*—125-150 with numerous buds.

*Lastingness of individual blooms on the plant.*—About 10 days.

*Fragrance.*—None.

Bud (just before opening/showing color):

*Color.*—RHS 59A.

*Length.*—1.0 cm.

*Width.*—0.6 cm.

*Shape.*—Conical, penta-shape.

Corolla:

Immature inflorescence:

*Diameter.*—1.4-1.6 cm.

*Color of petals, upper surface.*—RHS 59A.

*Lower surface.*—RHS 59A.

Mature inflorescence:

*Flower diameter.*—1.7-2.0 cm.

*Depth.*—0.7-0.8 cm.

*Petal color, upper surface.*—RHS 60A.

*Petal color, lower surface.*—RHS N155B whitish to RHS 59A.

*Veins color, upper surface.*—Darker than RHS 60A.

*Veins color, lower surface.*—Darker than RHS 59A.

*Length of petal.*—0.9 cm.

*Width of petal.*—0.7 cm.

*Shape.*—Orbicular, round to obovate.

*Apex shape.*—Ovate to obovate.

*Margin.*—Entire.

*Venation pattern.*—Bowed, parallel.

*Petal texture, upper surface.*—Glabrous.

*Lower surface.*—Glabrous.

Calyx:

*Quantity.*—5.

*Color, upper surface.*—RHS 137A/D.

*Color, lower surface.*—RHS 147A.

*Length.*—0.4 cm.

*Width.*—0.3 cm.

*Shape.*—Hastate, subulate.

*Apex shape.*—Acute.

*Base.*—Fused, deltoid.

*Margins.*—Entire.

*Texture, upper/inner surface.*—Smooth.

*Texture, lower/outer surface.*—Lower: glandular, puberulous; Up: glabrous.

Reproductive organs:

*Gynoecium.*—

*Pistil quantity.*—2.

*Pistil shape.*—Each style has a threadlike pistil shape.

*Length.*—0.5 cm.

*Style color.*—RHS 143B.

*Style length.*—0.35 cm.

*Stigma color.*—RHS 143B.

*Stigma shape.*—Spatulate.

*Ovary color.*—RHS 152C/D.

*Ovary height.*—0.5 cm.

*Ovary width.*—0.3 cm.

*Androecium.*—

*Stamens, quantity.*—10.

*Stamens, shape*.—Threadlike.
*Color of filaments*.—RHS 143A.
*Length filaments*.—0.5 cm.
*Anther color*.—RHS 22C, mottled with anthocyanins of about RHS N34C.
*Anther length*.—0.1 cm.
*Anther shape*.—Oval.
*Color of pollen*.—RHS 12B.
*Pollen amount*.—Moderate.
*Fertility/seed set*.—Neither seed nor fruit production has been observed to date.
*Disease/pest resistance*.—Resistance to pathogens and pests common to *Saxifraga* has not been observed.
*Drought tolerance and cold tolerance*.—Hardy perennial. Tolerates high temperature to at least 30 degrees C. Tolerates low temperatures to minus 15 degrees C. No specific drought tolerance has not been observed.

What is claimed is:

1. A new and distinct variety of *Saxifraga* plant named 'SAXZ0014' substantially as illustrated and described herein.

* * * * *